United States Patent [19]
Hoebel

[11] Patent Number: 5,677,943
[45] Date of Patent: Oct. 14, 1997

[54] X-RAY FILTER

[75] Inventor: Peter Hoebel, Buckenhof, Germany

[73] Assignee: Siemens Aktiengesellschaft, Munich, Germany

[21] Appl. No.: 704,106

[22] Filed: Aug. 28, 1996

[30] Foreign Application Priority Data

Sep. 15, 1995 [DE] Germany .................. 195 34 292.5

[51] Int. Cl.⁶ .................................................. G21K 3/00
[52] U.S. Cl. ........................ 378/156; 378/158; 378/159
[58] Field of Search .................................. 378/156, 157, 378/158, 159, 161, 145

[56] References Cited

U.S. PATENT DOCUMENTS

| | | | |
|---|---|---|---|
| 2,216,326 | 10/1940 | Smith | 378/159 X |
| 2,506,342 | 5/1950 | Burke | 378/158 |
| 3,717,768 | 2/1973 | Edholm et al. | 378/156 |
| 4,006,361 | 2/1977 | Schriber | 378/158 |
| 5,278,887 | 1/1994 | Chiu et al. | 378/156 |
| 5,287,396 | 2/1994 | Stegehuis | 378/156 X |
| 5,365,567 | 11/1994 | Ohtsuchi et al. | 378/156 |

*Primary Examiner*—David P. Porta
*Attorney, Agent, or Firm*—Hill, Steadman & Simpson

[57] ABSTRACT

An x-ray filter which produces a uniform distribution of the image contrast and the image brightness, with an optimally reduced skin dose has a pre-filter for the total x-ray beam and an edge filter, which leaves free a central region of the x-ray beam. The pre-filter is made of a material having an atomic number less than 60, such as copper, and the edge filter is made of a material having an atomic number between 64 and 77.

3 Claims, 1 Drawing Sheet

X-RAY FILTER

BACKGROUND OF THE INVENTION

1. Field of the Invention

The present invention is directed to an x-ray filter, of the type attached in front of an x-ray source for filtering x-rays emitted by the x-ray source, in an x-ray diagnostic apparatus.

2. Description of the Prior Art

In an x-ray diagnostic apparatus, filters are additively used for the prescribed filtering of the x-rays, for the reduction of the skin input dose, particularly of the low-energy radiation portion. Filters of this type are arranged on the x-ray source. The x-ray spectrum is thus shifted in the direction of higher energy, at the same x-ray tube voltage. The contrast in the representation of vessels inevitably suffers as a result.

SUMMARY OF THE INVENTION

An object of the present invention is to provide an x-ray filter which produces a brightness impression in the x-ray image that is approximately equal between the central region and the edge region, produces a contrast impression in the image that is uniform, and which reduces the skin dose is reduced to a minimum.

The above object is achieved in accordance with the principles of the present invention in an x-ray filter having a pre-filter which filters a totality of the x-ray beam emitted from the x-ray source, and an edge filter which leaves a central region of the x-ray beam free, the pre-filter being formed of a material having an atomic number less than 60, and the edge filter being formed of a material having an atomic number between 64 and 77.

In the invention, a central field having the necessary imaging dose rate is used, and the remaining edge is provided with a higher filtering, so that in this region the skin exposure is further reduced. The combination of materials brings about a uniform brightness and contrast distribution in the image and an optimal reduction of the skin dose.

DESCRIPTION OF THE PREFERRED EMBODIMENTS

Figure 1:
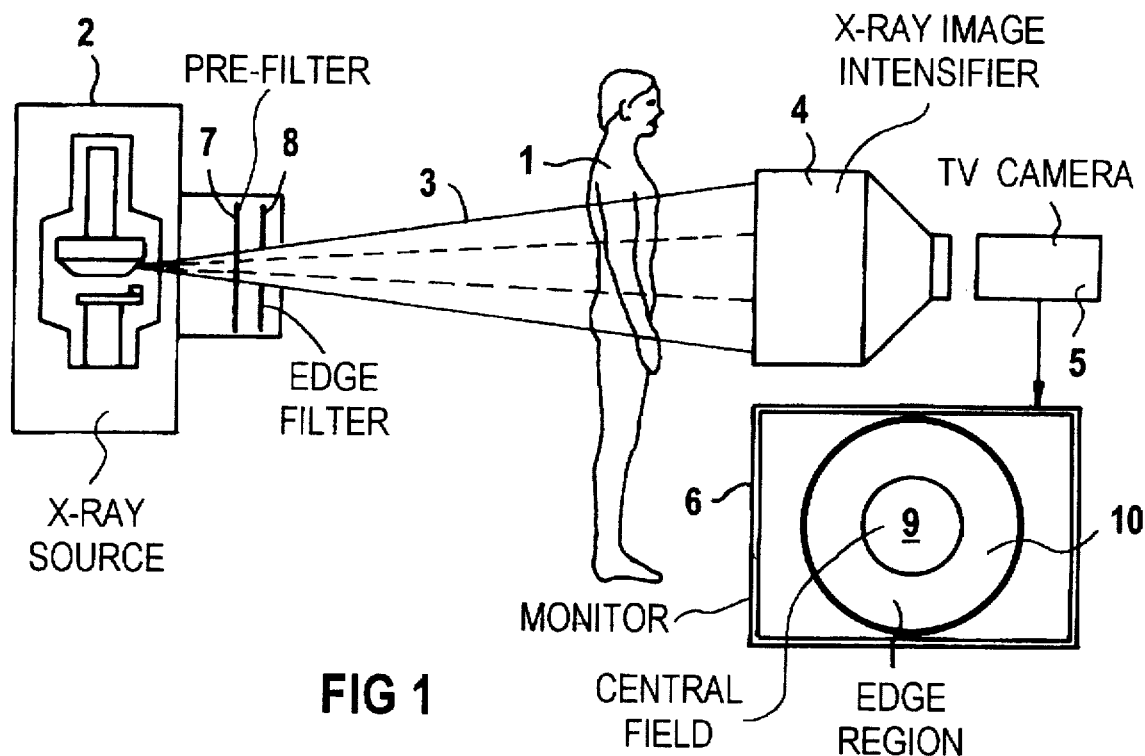
FIG. 1 shows an x-ray diagnostic apparatus having an x-ray filter according to the invention.

FIG. 1 shows a patient 1, transirradiated by the x-ray beam 3 emanating from an x-ray source 2. The x-ray beam 3 strikes an x-ray image intensifier 4, after having traversed the patient 1, and the output image of the x-ray image intensifier 4 is recorded by a television camera 5 and reproduced on a monitor 6.

An inventive x-ray filter is arranged in the housing of the primary radiation screen of the x-ray source 2, which filter consists of a pre-filter 7 and an edge filter 8. The edge filter 8 surrounds but leaves free a central, diagnostically important field 9 in the x-ray image. A limited diagnosis based on the x-ray image is likewise possible within the edge region 10, since here, for reducing the skin exposure, a higher filtering is present, which produces a still visible, though darker, image. The pre-filter 7 is preferably made of copper. The edge filter 8 is made from an element having an atomic number from 64 to 77, preferably 71 to 75. The material of the edge filter 8 meets the above-described requirements of uniform image contrast and uniform brightness, as well as an optimal reduction of the skin dose, and is easily workable. The material has a strong change of x-ray absorption in the energy region between 50 and 80 keV.

The combination of copper and tantalum or copper or tungsten has been found to have a favorable effect on the image parameters. An improvement is achieved particularly in the high x-ray tube voltage region, where the contrast fundamentally decreases.

Figure 2:
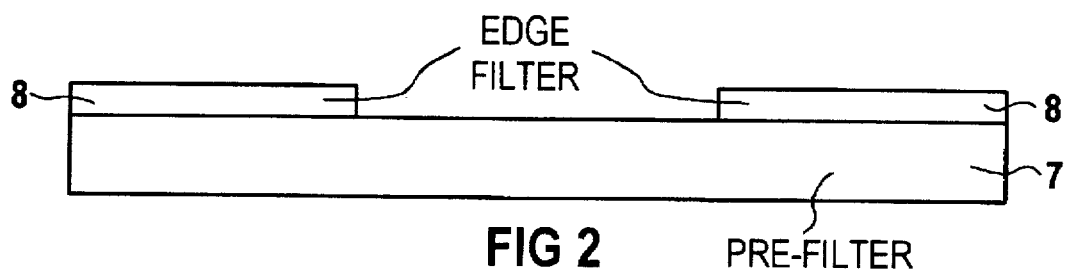
FIGS. 2 and 3 respectively show side views of two examples of an x-ray filter according to the invention.

FIG. 2 shows an example of a filter design in which the pre-filter 7 supports the edge filter 8. The thickness of the pre-filter 7 is, for example, from 0.1 to 0.3 mm, and the thickness of the edge filter 8 is 0.02 to 0.1 mm.

Figure 3:
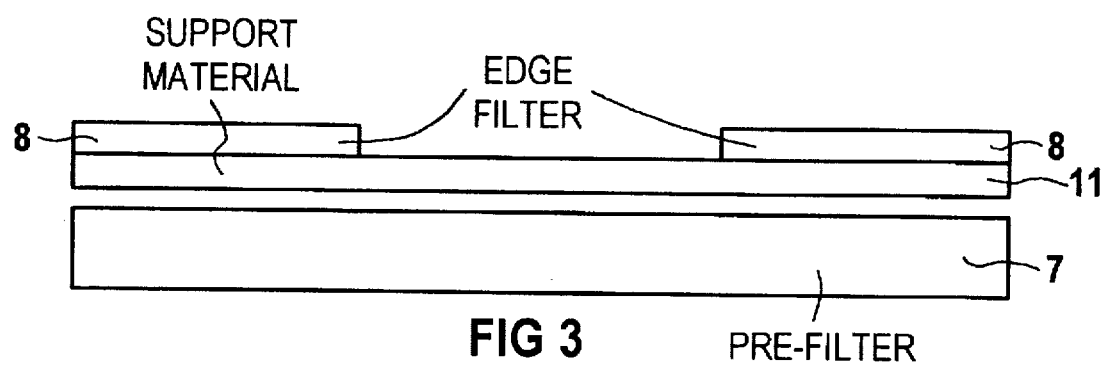

FIG. 3 shows an embodiment in which the pre-filter 7 and the edge filter 8 are separate from one another. The edge filter 8 is attached to a support material 11, e.g., aluminum.

The pre-filter 7 is made of a material having an atomic number less than 60, e.g. copper, and as noted above the edge filter 8 is made of a material having an atomic number between 64 and 77. The atomic number of the material for the pre-filter 7 is preferably less than 33.

Although modifications and changes may be suggested by those skilled in the art, it is the intention of the inventor to embody within the patent warranted hereon all changes and modifications as reasonably and properly come within the scope of his contribution to the art.

I claim as my invention:

1. An x-ray filter comprising a pre-filter, which filters a totality of an x-ray beam emanating from the x-ray source, and an edge filter that leaves a central region of the x-ray beam free, said pre-filter being comprised of a material having an atomic number less than 60 and the edge filter being comprised of a material having an atomic number between 64 and 77.

2. An x-ray filter according to claim 1, wherein the pre-filter is comprised of a material having an atomic number less than 33.

3. An x-ray filter according to claim 1, wherein the edge filter is comprised of a material having an atomic number between 71 and 75.

* * * * *